United States Patent [19]

Riley et al.

[11] 4,432,983

[45] Feb. 21, 1984

[54] CONFORMATIONALLY RESTRICTED HISTAMINE $H_2$-RECEPTOR ANTAGONISTS CONTAINING A TROPANE RING

[75] Inventors: Thomas N. Riley, Oxford, Miss.; Jerry Bagley, Athens, Ga.

[73] Assignee: Research Corporation, New York, N.Y.

[21] Appl. No.: 258,922

[22] Filed: Apr. 30, 1981

[51] Int. Cl.³ .................. A01N 31/46; C07D 451/04
[52] U.S. Cl. .................. 424/265; 546/125;
544/224; 544/333; 544/405
[58] Field of Search .................. 546/125; 424/265

[56] References Cited

U.S. PATENT DOCUMENTS 4,151,288 4/1979 Durant et al. .................. 424/270
4,321,378 3/1982 Dostert et al. .................. 424/265

*Primary Examiner*—Alan L. Rotman

*Attorney, Agent, or Firm*—Scully, Scott, Murphy & Presser

[57] ABSTRACT

Histamine $H_2$-receptor antagonists having the formula

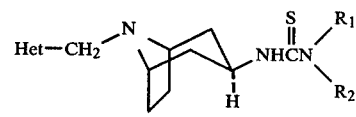

wherein $R_1$ represents $C_1$–$C_4$ alkyl or benzyl, $R_2$ represents hydrogen or $C_1$–$C_4$ alkyl, and Het represents an imidazole, pyrazole, pyrimidine, pyrazine, pyridazine, thiazole, isothiazole, oxazole, isoxazole, triazole, thiadiazole, benzimidazole, or furan ring either unsubstituted or substituted with a $C_1$–$C_4$ alkyl, hydroxyl, trifluoromethyl, benzyl, halogen, amino, or dimethylaminomethyl group are disclosed along with a synthetic method of producing such compounds and their use as gastric-acid-production inhibitors.

15 Claims, 2 Drawing Figures

CONFORMATIONALLY RESTRICTED HISTAMINE H$_2$-RECEPTOR ANTAGONISTS CONTAINING A TROPANE RING

BACKGROUND OF THE INVENTION

1. Field of the Invention

This invention relates to histamine H$_2$-receptor antagonists and more particularly to those antagonists having a tropane ring joining an imidazole-like ring to a thiourea group.

2. Description of the Prior Art

The pharmacological actions of histamine are mediated by at least two distinct classes of receptors. One receptor type, designated H$_1$, mediates histamine-induced contraction of smooth muscle of the small intestine and bronchi. A second receptor type, designated H$_2$, mediates the action of histamine in vivo stimulating gastric acid secretion and in vitro inhibiting contractions of the rat uterus and increasing the rate of beating of the guinea pig atrium. The receptors in these and other tissues are defined pharmacologically from the antagonists shown below, which selectively block the responses of the tissues to histamine stimulation.

Histamine H$_1$-Receptor Antagonists

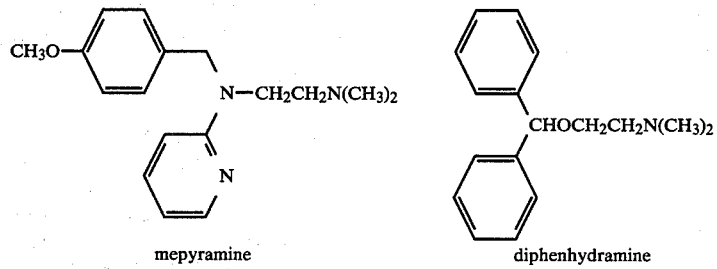

mepyramine diphenhydramine

Histamine H$_2$-Receptor Antagonists

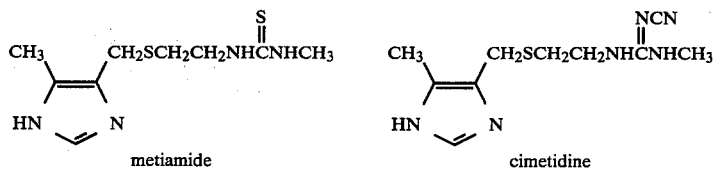

metiamide cimetidine

A clear distinction between the structural features of the H$_1$-antagonists and the H$_2$-antagonists is evident. The H$_1$-antagonists have aryl or heteroaryl rings that need not have any structural relationship to the imidazole ring of histamine, but possess a side chain which is positively charged at physiological pH. The aryl rings perhaps act in hydrophobic binding to the H$_1$-receptor and are also responsible for the inherent lipophilicity in these compounds (partition coefficient, P=2500 for diphenhydramine). Because of this liophilicity, H$_1$-antagonists are significantly distributed to the central nervous system. The H$_2$-antagonists resemble histamine in having an imidazole or similar unsaturated, heterocyclic ring but have an uncharged, though polar, side chain. These compounds are hydrophilic (P=2.5 for cimetidine) and like histamine (P=0.2) do not cross the blood-brain-barrier in appreciable concentrations. These substantial differences probably account for the considerable selectivity shown by the respective antagonists in distinguishing the two types of receptors.

Thus, it is assumed that H$_1$-receptor recognition is determined primarily by the ammonium group, while at H$_2$-receptors, affinity is determined by the imidazole or imidazole-like ring.

Heterocyclic ring variation of H$_2$-antagonists has usually involved other nitrogen containing aromatic rings such as thiazole and pyridine. Recently the prototype of a new class of H$_2$-antagonists structurally characterized by a furan ring system has been introduced. Ranitidine, shown below, was found to be a competitive antagonist, more potent than cimetidine

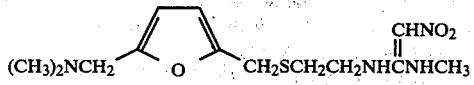

in the guinea pig isolated right atrium and in preventing histamine-induced gastric acid secretion in dogs. Thus an imidazole ring does not appear to be an essential recognition factor for the H$_2$-receptor, although structural similarity needs to be retained.

The first orally effective H$_2$-receptor antagonist to be developed was metiamide, whose structure has been previously given above. In clinical trials, metiamide was found to be effective in promoting the healing of peptic ulcers. However, metiamide was found to produce agranulocytosis through suppression of the cell-cycle of precursors of white blood cells. This effect has since been attributed to the thiourea moiety, since agranulocytosis was also encountered with the use of thioamide compounds to treat hyperthyroidism. This problem was overcome when the methylthiourea moiety was replaced with a methylnitriloguanidine moiety to give cimetidine.

Cimetidine was found to be a satisfactory replacement for metiamide, being initially a potent H$_2$-antagonist and, after extensive clinical trials, generally a safe agent for the treatment of peptic ulcer and associated gastrointestinal disorders. However, there have been a number of reports of various side effects, and, as experience with the drug mounts, newer adverse reactions are being reported in increasing frequency.

Accordingly, there exists a need for new and different H$_2$-receptor antagonists of demonstrated efficacy.

SUMMARY OF THE INVENTION

It is therefore an object of this invention to provide a histamine H$_2$-receptor antagonist having activity comparable to or greater than metiamide and cimetidine but with a different structure.

It is a further object of this invention to provide a histamine H$_2$-receptor antagonist having a specified conformation and relationship in space between an imidazole-like ring and a methylthiourea group.

These and other objects of the invention, as will hereinafter become more readily apparent, have been attained by providing a histamine H$_2$-receptor antagonist having the formula

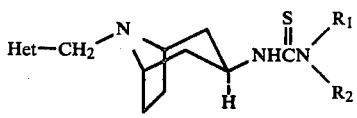

wherein R$_1$ represents C$_1$–C$_4$ alkyl or benzyl, R$_2$ represents hydrogen or C$_1$–C$_4$ alkyl, and Het represents an imidazole, pyrazole, pyrimidine, pyrazine, pyridazine, thiazole, isothiazole, oxazole, isoxazole, thiazole, thiadiazole, benzimidazole, or furan ring either unsubstituted or substituted with a C$_1$–C$_4$ alkyl, hydroxyl, trifluoromethyl, benzyl, halogen, amino, or dimethylaminomethyl group.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawing, wherein.

DESCRIPTION OF THE PREFERRED EMBODIMENTS

Figure 1A:
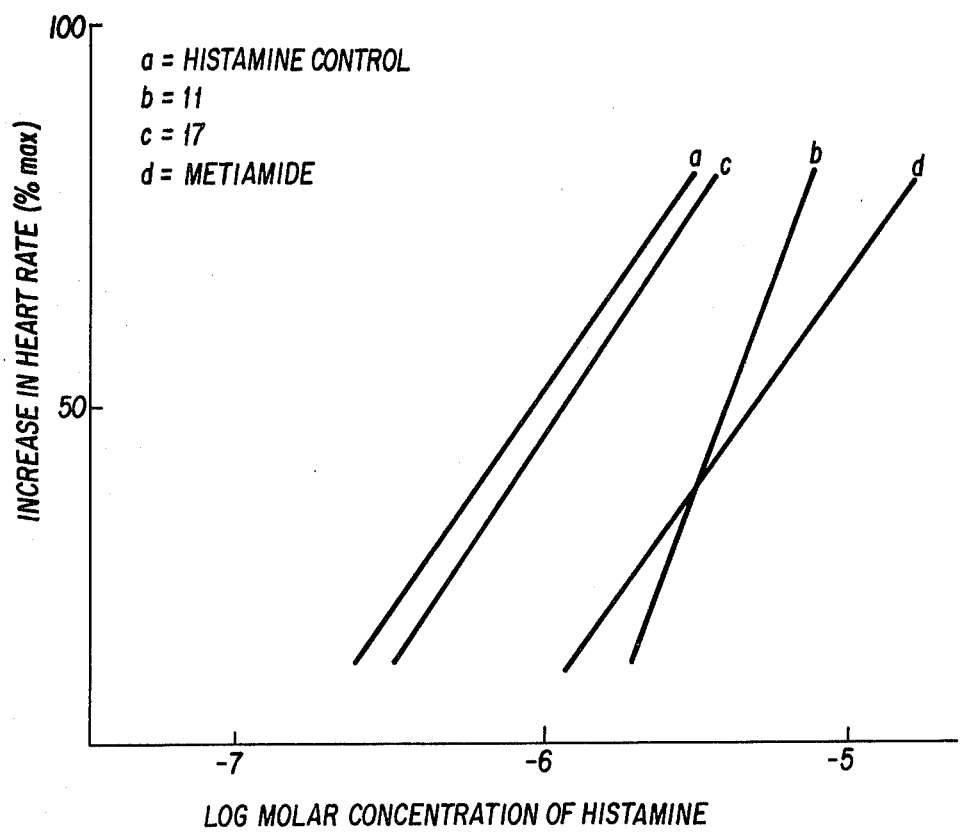
FIG. 1 shows dose-response curves from averaging data from separate determinations for histamine in the presence of known and proposed histamine H$_2$-receptor antagonists and related compounds.

Many unsaturated heterocyclic rings may replace the imidazole ring of histamine-like analogues with retention of at least some H$_2$ receptor antagonist activity. Many of these are disclosed in U. S. Pat. No. 4,151,288, and include pyrazole, pyrimidine, pyrazine, pyridazine, thiazole, isothiazole, oxazole, isoxazole, triazole, thiadiazole, and benzimidazole. More recently, a furan ring has been shown to exhibit significant histamine H$_2$-receptor antagonist activity. Preferred heterocyclic rings are furan, thiazole, and imidazole rings. The heterocyclic ring may be unsubstituted or may have one or more substituents selected from the group consisting of C$_1$–C$_4$ alkyl, hydroxyl, trifluoromethyl, benzyl, halogen, amino, or dimethylaminomethyl.

The terminal nitrogen of the thiourea moiety should be substituted with at least one lower (C$_1$–C$_6$) alkyl, alkenyl, or alkynyl group, or with a benzyl group. The substituent may be branched, cyclic, or linear. A second lower alkyl substituent is permissible. Preferred are single alkyl substituents, with methyl being most preferred. The thiourea nitrogen attached to the 3$\beta$-position of the tropane ring should be a secondary nitrogen.

Substitution on the methylene joining the imidazole-like ring to the tropane nitrogen is not permitted because it would cause steric hinderence. However, any of the tropane carbons not directly involved in covalent bonding to the unsaturated, heterocyclic ring moieties may have a hydrogen replaced by an organic substituent, subject only to the provisos that the substituent does not change the thermodynamic stability of the chair conformation of the 6-membered ring of tropane to make it less stable than the corresponding boat conformation and that the steric bulk of the organic substituent is not larger than a benzyl group. By organic substituent is meant any covalently bonded carbon-containing or non-carbon-containing, e.g., hydroxy or halogen, substituent found in organic chemistry. Preferred are C$_1$–C$_3$ alkyl substituents.

Compounds of the indicated formula may be synthesized by standard methods of organic chemistry. One such general method is outlined below and shown in reaction Scheme I.

Scheme I

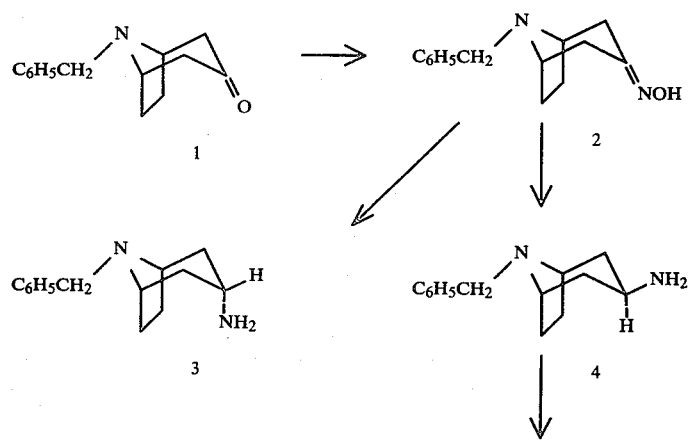

Scheme I

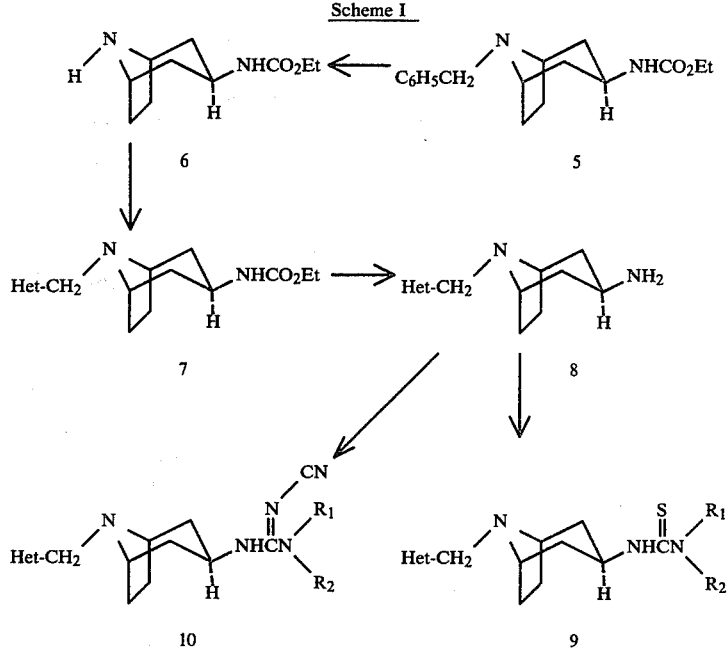

8-Benzylnortropinone (1) is synthesized by the method of Archer, U.S. Pat. No. 2,845,427, which is hereby incorporated by reference, by reacting 2,5-dimethoxytetrahydrofuran with 1,3-acetonedicarboxylic acid and benzylamine. Tropane rings having substituents at positions 2 and 4 can be made at this point from the tropinone molecule by using the carbonyl group to direct reactions to these positions as is well known in organic synthesis. Substituents can be introduced at other positions by a correct choice of starting compounds using the method of Archer. Oximination of 1 or related compounds using hydroxylamine hydrochloride and sodium bicarbonate give oxime 2. This compound can be selectively reduced by catalytic hydrogenation to give the axial amine 3, known as the 3α-isomer. The 3β-isomer 4 (equatorial amine) is easily obtained by reduction of the oxime with sodium in ethanol.

From this point forward, the stereochemistry at C-3 is fixed. Further reactions are illustrated with the 3β-isomer only, although similar reactions with the 3α-isomer occur in the same fashion.

Carbamoylation of amine 4 with ethyl chloroformate gives the protected 8-benzyl-3-aminotropane derivative 5, which can be debenzylated by hydrogenolysis to give 3-aminotropane derivative 6. Amide deviations may also serve to protect the 3-amino nitrogen. Since only the 8-aza nitrogen is basic, this nitrogen can be easily alkylated to give a heterocyclic moiety attached to the tropane ring using standard methods of organic synthesis. An example of a suitable method is refluxing an appropriate halomethyl-substituted heterocyclic compound with sodium carbonate or a similar acid-trapping agent in an alcohol solvent. For example, 5-methyl-4-imidazolylmethylchloride can be used as an N-alkylating agent. This compound can be prepared from the corresponding alcohol with concentrated HCl. The alcohol can be prepared by lithium aluminum hydride reduction of the commercially available ester, ethyl 5-methyl-4-imidazole carboxylate. Similar preparations of appropriate heterocyclic precursors are easily carried out from available starting materials by those of ordinary skill in the art of organic synthetic chemistry. Carboxylic acid derivatives of heterocyclic rings are generally readily available. These may be used in a reaction as outlined above, or can be converted into an amide or nortropane, which is then reduced.

The 3-amino protecting group may be removed from compound 7 by acid hydrolysis to give the free amine 8, now having an imidazole or similar heterocyclic ring attached to the 8-aza nitrogen through a methylene group. Treatment of this amine with an alkyl or benzyl isothiocyanate gives the desired substituted thiourea 9. This same amine may be treated successively with dimethylcyanodithioimidocarbonate and an alkyl or benzyl amine to give a substituted nitriloguanidine (10) if desired. Alternately, substituted thioureas can be prepared by reacting amine 8 with phosgene to give an isocyanate, reacting the isocyanate with a primary or secondary amine to give a substituted urea, and converting the urea to a thiourea.

N-Methyl-N'-[8-(5-methylimidazol-4-yl) methyl-1αH,5αH-nortropane-3β-yl]thiourea (compound 11) and several related compounds where synthesized as described above and were tested for histamine H2-receptor antagonist activity using a standard assay involving guinea pig heart tissue. This test is based on the experimentally demonstrated fact that only H2-receptors are found in the right atrium of the guinea pig heart. Stimulation with histamine increases the sinus rate of the isolated right atrium while H2-receptor antagonists counteract this increase. Compound 11 exhibited approximately the same antagonist activity as metiamide, while the 3α-isomer and the analogous compounds having the thiourea replaced with methylnitriloguanidine did not exhibit significant activity. In addition, none of these compounds demonstrated significant H1-antihistiminic activity when they were tested for such activity in a standard assay procedure using isolated guinea pig ileum.

The principal use anticipated for compounds of the present invention is in the treatment of peptic ulcers.

Because of its similar activity to metiamide, compound 11 and related compounds having different imidazole-like heterocyclic rings should be able to replace metiamide at the same dosage levels presently established for use of metiamide and compounds related to metiamide in a similar manner. Such compounds and dosage levels are discussed in U.S. Pat. No. 4,151,288, which is hereby incorporated by reference.

A suitable dosage level for inhibiting gastric acid production would be from about 0.1 to about 250 μmole antagonist/kg of body weight for animals or humans, preferably about 1 to about 25 μmole/kg. A preferred manner of administration and a preferred dosage for humans is oral ingestion of 25 to 250 mg of antagonist from one to four times daily. Parenteral administration is also acceptable.

The histamine $H_2$-receptor antagonists of the present invention may be used in the form of pharmaceutical compositions comprising the antagonist as the active ingredient and a pharmaceutically acceptable carrier.

The pharmaceutical carrier employed may be either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 10 mg to about 1000 mg, preferably from about 10 mg to about 250 mg and most preferably from about 25 mg to about 125 mg.

The active ingredient will preferably be administered in equal doses one to four times per day. The daily dosage regimen will preferably be from about 25 mg to about 1000 mg, most preferably from about 200 mg to about 800 mg.

For therapeutic use, the pharmacologically active compounds of the present invention will normally be administered as a pharmaceutical composition comprising as the only or an essential active ingredient at least one such compound in the basic form or in the form of an addition salt with an acid suitable to form a pharmaceutically acceptable salt and in association with a pharmaceutically acceptable carrier therefor. Such addition salts include those with hydrochloric, hydrobromic, hydriodic, sulphuric, citric, and maleic acids.

Other pharmacologically active compounds may in certain cases be included in the composition. The composition will be made up most advantageously in a dosage unit form appropriate to the desired mode of administration, for example as a tablet, capsule, injectable solution.

The above disclosure generally describes the present invention. A more complete understanding can be obtained by reference to the following specific examples, which are provided herein for purposes of illustration only and are not intended to be limiting unless otherwise indicated.

EXAMPLE 1

Synthesis of N-Methyl-N'-[8-(5-methylimidazol-4-yl)methyl-1αH,-5αH-nortropane-3β-yl]thiourea (11)

8-Benzyl-1αH,5αH-nortropan-3-one oxime (2)

To a solution of 8-benzylnortropinone (1, 50.0 g, 0.232 mol) in 200 mL of 95% EtOH, was added in one portion a solution of $NH_2OH.HCl$ (32.2 g, 0.464 mol) in 200 mL of $H_2O$. Sodium bicarbonate (39.0 g, 0.464 mol) was added in portions, and the mixture was heated on a steam bath for 30 min. After stirring at ambient temperature for 18 h, the white precipitate was collected by filtration, washed with $H_2O$ (3×200 mL), and dried in vacuo to give 48.6 g (91%) of 2: mp 122°–123°; Ir (KBr) 1656 cm$^{-1}$ (oxime C=N); NMR (CDCl$_3$) δ 3.35–3.65 (m, 2, C$_1$H and C$_5$H), 3.82 (s, 2, C$\underline{H}_2$C$_6$H$_5$), 7.35–7.82 (m, 5, aromatic). The oxime was used in the subsequent reduction procedures without further purification. A small analytical sample was recrystallized from 95% EtOH, mp 122°–123° (colorless prisms); MS, m/e 230 (M+).

Anal. Calcd for $C_{14}H_{18}N_2O$: 73.01; H, 7.88; N, 12.17. Found: C, 73.29; H, 7.92; N, 12.04.

8-Benzyl-3β-amino-1αH-nortropane (4)

To a solution of 2 (25 g, 0.109 mol) in 200 mL of EtOH were added pieces of Na (37 g, 1.61 g.at) as needed to maintain a brisk reflux. During this time an additional 100 mL EtOH was added in order to ensure dissolution of the NaOEt. Upon dissolution of the Na, the reaction mixture was refluxed for 16 h, cooled, and 500 mL of H$_2$O was added to dissolve the precipitated NaOEt. The majority of the EtOH was evaporated and the residual aqueous mixture was chilled and carefully acidified with conc HCl. The acidic solution was washed with Et$_2$O and made basic with 12 N NaOH. The free base was extracted with Et$_2$O (3×200 mL) and the combined ethereal extracts were washed with H$_2$O (3×100 mL) and dried (Na$_2$SO$_4$). Evaporation of solvent yielded a colorless oil which was distilled to give 15.5 g (66%) of 4: bp 100°–114° (0.107 kPa); NMR (CDCl$_3$) δ 1.05 (s, 2, N$\underline{H}_2$), 3.92 (nonet, 1, J=7, 11 Hz, C$_3$H), 3.05–3.30 (m, 2, C$_1$H and C$_5$H), 3.55 (s, 2, C$\underline{H}_2$CH$_6$H$_5$), 7.07–7.50 (m, 5, aromatic). The dioxalate salt was prepared by adding a hot ethanolic solution of the free base to a boiling ethanolic solution of 2 mole-equivalents of oxalic acid and cooling: mp 136°–140° (EtOH—H$_2$O); MS, m/e 216 (M+).

Anal. Calcd for $C_{14}H_{20}N_2.2\ C_2H_2O_4.0.5\ H_2O$: C, 53.33; H, 6.22; N, 6.91. Found: C, 53.25; H, 6.35; N, 6.81.

8-Benzyl-3β-(N-carbethoxyl)amino-1αH,5αH-nortropane (12)

To a chilled suspension of 4 (14.1 g, 0.065 mol), and anhydrous Na$_2$CO$_3$ (30.0 g, 0.283 mol) in 100 mL CH$_3$CN was added in a dropwise manner a solution of ClCO$_2$Et (7.8 g, 0.065 mol) in 25 mL of CH$_3$CN. The reaction mixture was refluxed for 16 h and carefully filtered while hot to avoid precipitation of crude 12. The solvent was evaporated to give a brown oil which was taken up in 10% HCl. The acidic solution was washed with Et$_2$O and basified with 12 N NaOH. The free base was extracted with CHCl$_3$ (3×100 mL) and the combined organic extracts were washed with H$_2$O (3×50 mL) and dried (Na$_2$SO$_4$). After evaporation of CHCl$_3$, crude 12 was recrystallized from hexane-pet ether yielding 14.1 g (81%) of 12 (colorless flakes): mp 101°–102°; IR (KBr) 1688 cm$^{-1}$ (carbamate C=O); NMR (CDCl$_3$) δ 1.21 (t, 3, J=7 Hz, COCH$_2$C$\underline{H}_3$), 3.05–3.35 (m, 2, C$_1$H and C$_5$H), 3.52 (s, 2, C$\underline{H}_2$C$_6$H$_5$), 4.08 (q, 2, J=7 Hz, COC$\underline{H}_2$CH$_3$), 7, 7.10–7.42 (m, 5, aromatic); MS, m/e 288 (M+).

Anal. Calcd for C$_{17}$H$_{24}$N$_2$O$_2$: C, 70.80; H, 8.39; N, 9.72. Found: C, 70.95; H, 8.50; N, 9.72.

3β-(N-Carbethoxy)amino-1αH,5αH-nortropane (13)

A solution of 12 (12.5 g, 0.043 mol) in 100 mL EtOH and 5 mL HOAc was treated with 10% Pd/C (1.2 g), and hydrogenated (2.45 kg/m) at room temperature for 24 h. The reaction mixture was filtered through Celite and concentrated in vacuo. The residual oil was taken up in 10% HCl and the acidic solution washed with Et$_2$O. The free base was liberated with 12 N NaOH, extracted with CHCl$_3$ (3×50 mL), and the combined organic extracts washed with H$_2$O (3×25 mL) and dried (Na$_2$SO$_4$). The solvent was evaporated yielding a colorless oil which was distilled to give 6.6 g (77%) of 12: bp 104° (0.007 kPa); IR (liq film) 1710 cm$^{-1}$ (carbamate C=O); NMR (CDCl$_3$) δ 1.22 (t, 3, J=7 HZ, COCH$_2$C$\underline{H}_3$), 3.47–3.67 (m, 2, C$_1$H and C$_5$H), 4.10 (q, 2, J=7 Hz, COC$\underline{H}_2$CH$_3$). The oxalate salt was prepared in the usual manner, mp 171°–171.5° (EtOH); MS, m/e 198 (M+).

Anal. Calcd for C$_{10}$H$_{28}$N$_2$O$_2$·C$_2$H$_2$O$_4$: C, 49.99; H, 6.99; N, 9.72. Found: C, 50.02; H, 7.30; N, 9.64.

(5-Methylimidazol-4-yl)methylchloride hydrochloride (14)

A paste of ethyl 4-methyl-5-imidazolecarboxylate (37.5 g, 0.243 mol) and a little dry THF was added in portions to a stirred suspension of LiAlH$_4$ (12.0 g, 0.316 mol) in 1.0 L of dry THF under a flow of nitrogen. After refluxing for 4 h, the suspension was cooled in an ice-water bath and the excess LiAlH$_4$ destroyed with successive additions of 12 mL of H$_2$O, 12 mL of 15% NaOH, and 45 mL of H$_2$O. The white suspension was brought to room temperature (2 h) and filtered. After collecting the precipitate, it was digested in hot THF (500 mL), cooled, and filtered again. The total THF filtrate was concentrated in vacuo, the residual orange oil was dissolved in a minimum amount of EtOH, and 500 mL of hot EtOAc:Et$_2$O (3:2) was added. The solution was chilled yielding 15.0 g (55%) of (5-methylimidazol-4-yl)methanol as white prisms: mp 138° (lit. 138°). This material (9.6 g, 0.086 mol) was dissolved in 50 mL of conc HCl and heated on a steam bath for 30 min. The acidic mixture was concentrated in vacuo to dryness and the solid dissolved in a minimum amount of EtOH. With the addition of a little dry Et$_2$O, 14 (8.5 g, 67%) precipitated as a white powder: mp 236°–237° (lit. 222°).

8-(5-Methylimidazol-4-yl)methyl-3β-(N-carbethoxy)amino-1αH,5αH-nortropane (15)

To a suspension of 13 (7.6 g, 0.038 mol), anhydrous Na$_2$CO$_3$ (20.0 g, 0.189 mol) and 100 mL of MeOH was added with a disposable pipet a solution of 14 (7.0 g, 0.042 mole) in 40 mL MeOH. The reaction mixture was refluxed for 2 h, cooled, filtered, and the solvent evaporated to give a brown foam. The residue was partitioned between 50 mL of H$_2$O and 100 mL of CHCl$_3$:MeOH (5:1). The organic extract was dried (Na$_2$SO$_4$) and concentrated in vacuo to a brown foam which when digested in hot CH$_3$CN gave 15 as a white powder (7.2 g, 65%): mp 186°–187°; IR (KBr) 1682 cm$^{-1}$ (carbamate C=O); NMR (DMSO—d$_6$) δ 1.16 (t, 3, J=7 Hz, COCH$_2$C$\underline{H}_3$), 2.11 (s, 3, Im—CH$_3$), 3.33 (s, 2, Im—C$\underline{H}_2$—), 3.91 (q, 2, J=7 Hz, COC$\underline{H}_2$CH$_3$), 7.18 (s, 1, Im—C$_3$H). Compound 15 was used in the next step without further purification. A small analytical sample was recrystallized from CH$_3$CN, mp 184.5°–185°; MS, m/e 292 (M+).

Anal. Calcd for C$_{15}$H$_{24}$N$_4$O$_2$: C, 61.62; H, 8.27; N, 19.16. Found: C, 61.50, H, 8.49; N, 19.05.

8-(5-Methylimidazol-4-yl)methyl-3β-amino-1αH,5αH-nortropane (16)

A solution of 15 (6.9 g, 0.024 mol) and 48% HBr (50 mL, distilled over SnCl$_4$) was refluxed for 30 min. The solution was then concentrated to dryness. The residual orange solid was then digested in hot i-PrOH and stirred overnight at ambient temperature. The suspension was filtered and the solid dried in vacuo to give 9.8 g (90%) of 16·3 HBr (cream-colored powder): mp >300° (dec); NMR (D$_2$O) δ 2.52 (s, 3, Im—C$\underline{H}_3$), 3.95 (nonet, 1, J=7, 11 HZ, C$_3$H), 4.25–4.45 (m, 2, C$_1$H and C$_5$H), 4.53 (s, 2, Im—C$\underline{H}_2$—), 8.83 (s, 1, Im—C$_3$H). Compound 16·3 HBr was used in the next step without further purification. A small analytical sample was recrystallized from i-PrOH/MeOH as colorless beads, mp >300° (dec); MS, m/e 220 (M+).

Anal. Calcd for C$_{12}$H$_{20}$N$_4$·3 HBr·2 H$_2$O: C, 28.88; H, 5.45; N, 11.23. Found C, 28.79; H, 5.73; N, 11.42.

N-Methyl-N'-[8-(5-methylimidazol-4-yl)methyl-1αH,5αH-nortropan-3β-yl]thiourea (11)

A solution of 16·3 HBr (9.9 g, 22.0 mmol) in H$_2$O (75 mL) was filtered and made basic with K$_2$CO$_3$ (7.9 g, 55.0 mmole). The basic solution was concentrated to dryness and the residue digested in hot i-PrOH. The suspension was cooled, filtered, and concentrated in vacuo to give the free base 16 (4.7 g, 22.0 mmol) as a white solid. A solution of this material in 75 mL of EtOH was prepared, to which was added methyl isothiocyanate (1.7 g, 23.0 mmol) in EtOH (25 mL). The reaction mixture was gently refluxed for 30 min, cooled, and concentrated in vacuo to a white foam. This material was digested in hot CN$_3$CN and filtered without cooling to give 3.7 g (60%) of 11 as a white powder, mp 147°–150°. The hot filtrate on sitting overnight gave 0.5 g more of 11 as white plates (total yield 68%): mp 155°–158°; IR (KBr) 1555 cm$^{-1}$ (thiourea C=S); NMR (DMSO—d$_6$) δ 2.16 (s, 3, Im—CH$_3$), 2.84 (d, 3, J=4 Hz, NHC$\underline{H}_3$), 4.12–4.35 (m, 2, C$_1$H and C$_5$H), 3.45 (s, 2, Im—C$\underline{H}_2$—), 3.98–4.66 (m, 1, C$_3$H), 7.43 (s, 1, Im—C$_3$H).

Anal. Calcd for C$_{14}$H$_{23}$N$_5$S: C, 57.30; H, 7.90; N, 23.87; S, 10.97. Found: C, 56.93; H, 7.83; N, 23.55; S, 10.64.

EXAMPLE 2

Synthesis of
N-Methyl-N'-[8-(5-methylimidazol-4-yl)methyl-1αH,-5αH-nortropan-3α-yl]thiourea (17),
N''-Cyano-N-methyl-N'-[8-(5-methylimidazol-4-yl)methyl-1αH,5αH-nortropan-3α-yl]guanidine (18), and
N''-Cyano-N-methyl-N'-[8-(5-methylimidazol-4-yl)methyl-1αH,5αH-nortropan-3β-yl]guanidine (19)

Compound 17 (the 3α-isomer of compound 11) was synthesized in a manner similar to that shown in Example 1 for Compound 11. Compounds 18 and 19 (the corresponding analogues of Cimetidine) were synthesized from intermediate 16 and its 3α-isomer by successive reactions with dimethylcyanodithioimidocarbonate and methyl amine. None of these compounds demonstrated significant histamine antagonist activity ($H_1$ or $H_2$) in biological tests.

EXAMPLE 3

Determination of Histamine $H_2$-Receptor Antagonist Activity

Guinea pigs (Hartley strain) of either sex (400–700 g) were allowed at least two weeks acclimation period. The animals were housed two per cage in wire-meshed bottom stainless steel cages in animal quarters maintained on a 12 hour light:12 hour dark cycle with ambient temperature of approximately 24° C. Food (Ralston-Purina guinea pig chow #5025) and water were provided ad libitum.

The animals were stunned by a blow to the head and the heart was quickly removed and placed in Tyrode's solution (composition in g/L of distilled water: NaCl, 8.00; KCl, 0.20; $MgSO_4.7 H_2O$, 0.10; $CaCl_2$, 0.20; $NaH_2PO_4$, 0.05; $NaHCO_3$, 1.00; glucose, 1.00) at room temperature. All other tissue was carefully trimmed away, leaving only the right atrium. The base of the atrium was attached to a fixed pin in a 50 mL Magnus bath of the overflow type, while the atrial apex was similarly connected to a physiograph (Narco Bio-Systems) via a photoelectric force transducer (Narco Bio-Systems, sensitivity=0.05 g/cm). A 400 mg tension was constantly applied to the tissue. The Magnus bath was surrounded by water maintained at 37° C. with a constant temperature circulating pump. The bath was continually oxygenated (95% $O_2$, 5% $CO_2$) via a sintered glass gas delivery tube directly beneath the tissue support base.

Propanolol ($1 \times 10^{-6}$ M) was added to each preparation in order to eliminate the influence of endogenously stored catecholamine release. Following the addition of propanolol, test compound was added and the tissue was allowed to equilibrate for 30 minutes. After the equilibration period, cumulative doses of histamine dihydrochloride were added to the tissue bath via a 1.0 mL glass syringe equipped with a 1-inch 20-gauge needle. At least three doses of the agonist were added during the period in which 17–85 percent of the maximum histamine-induced chronotropic response was obtained. The total volume of histamine solution added did not increase the total bath volume more than 5 percent. The spontaneous heart rate was counted from the recorded tracing at the end of a 5-minute period following each addition of histamine.

Stock solutions (100 mM) of the free bases metiamide and cimetidine were prepared by dissolving 0.5 mmol of either in 0.46 mL of 1.23 N HCl, adding 1.0 mL of 0.1 N NaOH and water to 5.0 mL. Solutions of the test compounds were similarly prepared.

The increase in heart rate (percent of maximum response) was plotted versus the logarithm of the molar concentration of histamine. One tissue was used for each determination of the $ED_{50}$ of histamine, i.e., the effective dose required to cause a 50% increase in heart rate. Four separate determinations were made with the histamine control group, while three separate determinations were made for each compound. A straight line was fitted to the data points of each determination within each group by linear regression analysis. The slope and the $ED_{50}$ were calculated from the regression line, the slopes and $ED_{50}$ values of each group were averaged, and the standard deviations were calculated. Calculation of the linear regression gave values for the correlation coefficient (r) slope, average of x values, average of y values, and log $ED_{50}$. With this information a straight line representing a mean of the data from the separate determinations of each group could be plotted, i.e. a straight line passing through the mean x value and the mean y value and having the mean slope. The 95 percent confidence limits were calculated using the following formula: confidence limits = $\pm ts\sqrt{N}$ where t=Student's t value, s=standard deviation, and N=number of determinations. Differences between the histamine control, standards, and test compounds were determined by a one-way analysis of variance and, where indicated, individual t-test (Table I).

TABLE I

Evaluation of Compounds Related to Metiamide and Cimetidine for Histamine $H_2$-Receptor Antagonism.[a,b,c]

| Compound | Number of Tissues | $ED_{50}$ (95% CL) $\times 10^{-7}$ M | Slope (95% CL) |
|---|---|---|---|
| histamine control | 4 | 8.13 (4.07–14.8) | 0.63 (0.50–0.76) |
| metiamide[d] | 3 | 49.0 (30.9–77.6)[e] | 0.47 (0.41–0.53) |
| N—Methyl-N'—[8-(5-methylimidazol-4-yl)methyl-1αH,5αH—nortropan-3β-yl]thiourea (11)[d] | 3 | 40.7 (27.5–60.3)[e] | 0.99 (0.95–1.03)[e,f] |
| N—Methyl-N'—[8-(5-methylimidazol-4-yl)methyl-1αH,5αH—nortropan-3α-yl]thiourea (17)[d] | 3 | 11.0 (4.37–27.5) | 0.64 (0.18–1.10) |
| cimetidine[d] | 3 | 49.0 (43.7–55.0)[e] | 0.67 (0.28–1.06) |
| N''—Cyano-N—methyl- | 3 | 11.0 (5.01–24.0) | 0.64 (0.18–1.10) |

TABLE I-continued
Evaluation of Compounds Related to Metiamide and Cimetidine for Histamine $H_2$-Receptor Antagonism.[a,b,c]

| Compound | Number of Tissues | $ED_{50}$ (95% CL) $\times 10^{-7}$ M | Slope (95% CL) |
| --- | --- | --- | --- |
| N'—[8-(5-methyl-imidazol-4-yl]-1αH,5αH—nortropan-3α-yl]]guanidine (18)[d] N"—Cyano-N—methyl-N'—[8-(5-methyl-imidazol-4-yl]-1αH,5αH—nortropan-3β-yl]]guanidine (19)[d] | 3 | 6.92 (0.22–138.0) | 0.58 (0.23–0.93) |

[a] Isolated guinea pig right atrium.
[b] Tissue bath contained $10^{-6}$ M propranolol.
[c] Correlation coefficients ranged from 0.82 to 0.97.
[d] Concentration of compound was $10^{-6}$ M.
[e] Significantly different from histamine control value (P <0.05).
[f] Regression line is not parallel with that of histamine control.

Figure 1B:
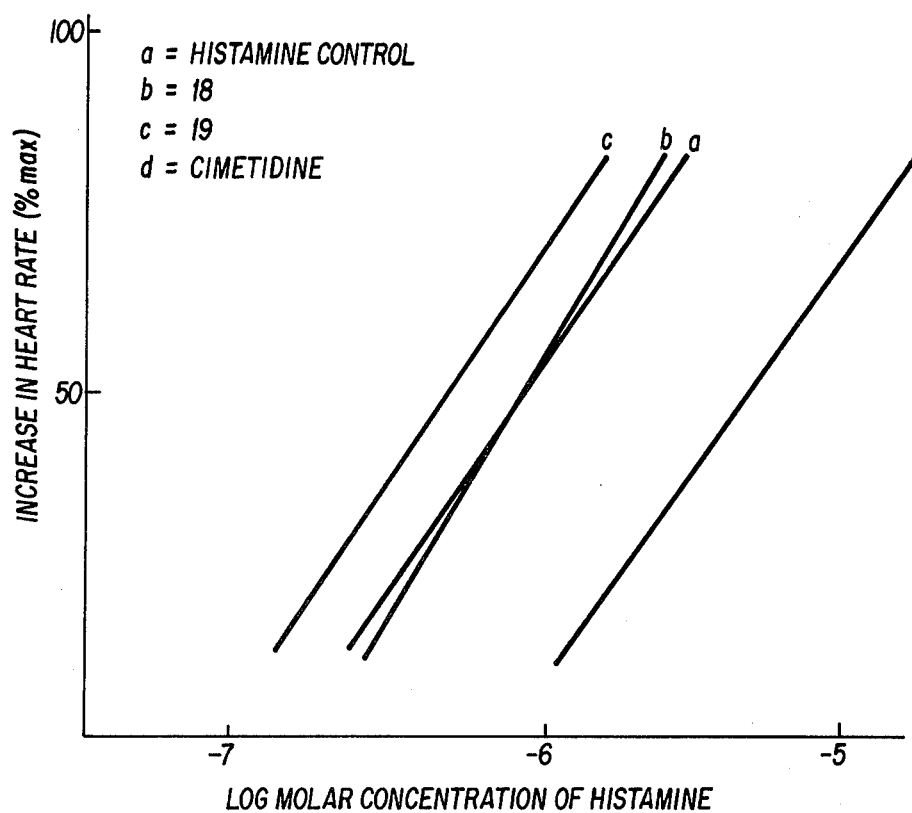

Previously reported $K_B$ (apparent dissociation constant) values for metiamide and cimetidine are $9.2 \times 10^{-7}$ M and $7.9 \times 10^{-7}$ M, respectively. Hence, tissue bath concentrations of $10^{-6}$ M metiamide and cimetidine were found to significantly increase the $ED_{50}$ of histamine on the right atrium from $8.13 \pm 1.55 \times 10^{-7}$ M to $49.0 \pm 12.0 \times 10^{-7}$ M in the case of each $H_2$-antagonist. The $K_B$ value of metiamide and cimetidine determined from these data using the equation $K_B = [B]/(\text{dose ratio} - 1)$, where [B] is the molar concentration of antagonist and dose ratio is the ratio of $ED_{50}$ values of agonist with and without test compound, was found to be $2.0 \times 10^{-7}$ M. The competitive nature of the antagonism by these compounds can be seen in the parallel shift of the dose-response curves of histamine induced by these agents (FIGS. 1A and 1B).

Since metiamide and cimetidine were shown to possess significant antagonism of the chronotropic effect of histamine at a $10^{-6}$ M concentration, this concentration was used for making comparisons of the effects on atrial tissue of the test compounds to the standards. The results of these experiments revealed that, among the four test compounds, only the β-tropyl analog of metiamide (11) was active. A $K_B$ value was not calculated since the utility of these values is contingent upon the presence of competitive inhibition. The slope of the histamine log dose-response curve in the presence of 11 is significantly steeper (P<0.05) than for metiamide (FIG. 1A). The observation that the histamine log dose-resonse curve is shifted to higher concentrations by 11 suggests that there is a competitive component to the $H_2$-receptor antagonism exerted by this compound but the non-parallel slope of the curve is difficult to interpret. A non-competitive component of the antagonism would be expected to depress the curve. A 100 percent maximum response was obtained with histamine in the presence of 11, as was the case with the standard antagonists and the other test compounds. An additional experiment adding only 11 to the bath was carried out in an attempt to detect possible interfering agonist activity. However, cumulative additions of 11 ($10^{-5}$ to $10^{-3}$ M) were without effect on heart rate or force of the isolated right atrium. The reason for this atypical curve is not known. Although there is an absence of parallelism in the curve for histamine in the presence of 11, the $ED_{50}$ value of 11 is similar to that of metiamide.

The α-tropyl analog of metiamide (17) was without any significant activity at a $10^{-6}$ M concentration as compared to the high $H_2$-antagonist activity of the β-isomer. This suggests that the histamine $H_2$-receptor is highly stereoselective in its recognition of the thiourea class of antagonists.

The α- and β-tropyl analogs of cimetidine (18 and 19) were without significant activity at the test concentration of $10^{-6}$ M. Therefore, the tropyl group linking the imidazole ring to the thiourea moiety in the compounds of the present invention must be functioning in a different manner from the thioether that forms the central portion of the cimetidine and metiamide molecules. Metiamide and cimetidine have similar activities and similar activities would be expected for compounds 11 and 19 if the tropyl bridging group were equivalent to the thioether bridging group.

EXPERIMENT 4

Determination of Histamine $H_1$-Receptor Antagonist Activity

Compounds 11, 17, 18, and 19 were screened for $H_1$-antihistaminic activity by observing if any significant blockage of histamine-induced contraction of the isolated guinea pig ileum occurred. After sacrificing the guinea pig by a blow to the head, longitudinal segments of the terminal ileum were removed and freed of mesentery and blood vessels. The same apparatus and physiological solution employed in the atrial preparation were used in these experiments. The tissue was loaded with a 500 mg tension and adjustments were made repeatedly until the baseline stabilized at this tension load. Atropine sulfate ($1 \times 10^{-6}$ M) was added to block the influence of endogenously stored acetylcholine and the preparation was allowed to equilibrate for 15 minutes before any other compounds were added. The concentration of test compound used was $1 \times 10^{-6}$ M. Visual determination of the absence of significant reduction in histamine-induced contractions of the ileum in the presence and absence of each test compound was interpreted as an absence of $H_1$-antihistaminic activity. Generally, $H_1$-antagonism is considered to be potent if significant reduction in ileal contractility occurs with antagonist concentrations less than micromolar.

The invention now being fully described, it will be apparent to one of ordinary skill in the art that many changes and modifications can be made thereto without departing from the spirit or scope of the invention as set forth herein.

What is claimed as new and intended to be covered by Letters Patent is:

1. A histamine $H_2$-receptor antagonist, having the formula

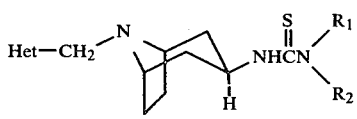

wherein
$R_1$ represents $C_1$–$C_4$ alkyl or benzyl,
$R_2$ represents H or $C_1$–$C_4$ alkyl, and
Het represents an imidazole ring either unsubstituted or substituted with a $C_1$–$C_4$ alkyl, hydroxyl, trifluoromethyl, benzyl, halogen, amino or dimethylaminomethyl group.

2. The histamine $H_2$-receptor antagonist of claim 1, wherein a tropane carbon not involved in covalent bonding to Het has a hydrogen replaced by an organic substituent, subject only to the proviso that the steric bulk of said substituent is not larger than a benzyl group.

3. The histamine $H_2$-receptor antagonist of claim, 1 wherein $R_2$ represents H.

4. The histamine $H_2$-receptor antagonist of claim 3, wherein $R_1$ represents methyl.

5. The histamine $H_2$-receptor antagonist of claim 4, wherein Het represents a 5-methylimidazol-4-yl radical.

6. A method of inhibiting histamine $H_2$-receptors which comprises administering to a human or animal in need of inhibition of said receptors an effective amount of the antagonist of claim 1.

7. The method of claim 5, wherein said antagonist is administered at a dosage of 1 to 250 μmole/kg.

8. The method of claim 5, wherein said antagonist is administered orally.

9. A histamine $H_2$-receptor antagonist comprising the antagonist of claim 1 or a pharmaceutically acceptable salt thereof in an effective amount and a pharmaceutically acceptable carrier.

10. The histamine $H_2$-receptor antagonist of claim 9, wherein said antagonist or said salt is present in a unit dose.

11. The histamine $H_2$-receptor antagonist of claim 9, wherein said antagonist or said salt is present in an amount of from about 10 mg to about 1000 mg.

12. The histamine $H_2$-receptor antagonist of claim 1, wherein Het represents an imidazole ring either unsubstituted or substituted by a lower alkyl group.

13. A histamine receptor antagonist comprising the antagonist of claim 1 or a pharmaceutically acceptable salt thereof in an effective amount and a pharmaceutically acceptable carrier.

14. The histamine $H_2$-receptor antagonist of claim 13, wherein said antagonist or said salt is present in a unit dose.

15. The histamine $H_2$-receptor antagonist of claim 13, wherein said antagonist of said salt is present in an amount of from about 10 mg to about 1000 mg.

* * * * *